(12) United States Patent
Dillinger

(10) Patent No.: US 8,939,992 B2
(45) Date of Patent: Jan. 27, 2015

(54) STEERABLE STONE BASKET

(71) Applicant: Boston Scientific Scimed, Inc., Maple Grove, MN (US)

(72) Inventor: Norman Dillinger, Elletssville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/670,241

(22) Filed: Nov. 6, 2012

(65) Prior Publication Data

US 2013/0066330 A1 Mar. 14, 2013

Related U.S. Application Data

(63) Continuation of application No. 12/213,265, filed on Jun. 17, 2008, now Pat. No. 8,328,819.

(60) Provisional application No. 60/960,950, filed on Oct. 22, 2007.

(51) Int. Cl.
*A61B 17/22* (2006.01)
*A61B 17/221* (2006.01)

(52) U.S. Cl.
CPC ....... *A61B 17/221* (2013.01); *A61B 2017/2212* (2013.01)
USPC ..................................................... 606/127

(58) Field of Classification Search
CPC .................. A61B 17/22; A61B 17/221; A61B 17/22031; A61F 2/01
USPC ............. 606/45–47, 106, 110, 113, 114, 127, 606/128, 200
See application file for complete search history.

(56) References Cited

U.S. PATENT DOCUMENTS

| 6,174,318 | B1 | 1/2001 | Bates et al. |
| 6,264,664 | B1 | 7/2001 | Avellanet |
| 6,872,211 | B2 | 3/2005 | White et al. |
| 8,182,508 | B2 | 5/2012 | Magnuson et al. |
| 2005/0119668 | A1 | 6/2005 | Teague et al. |
| 2005/0216031 | A1 | 9/2005 | White et al. |
| 2005/0251151 | A1 | 11/2005 | Teague |
| 2005/0261706 | A1 | 11/2005 | Cheng et al. |

FOREIGN PATENT DOCUMENTS

| EP | 0 195 444 A | 9/1986 |
| EP | 1 566 148 A | 8/2005 |

OTHER PUBLICATIONS

International Search Report for PCT/US2008/067452, mailed Oct. 1, 2008, 7 pages.
Written Opinion of the International Search Authority in PCT/US2008/067452, mailed Oct. 1,2008, 7 pages.

*Primary Examiner* — Ashley Fishback
(74) *Attorney, Agent, or Firm* — Bookoff McAndrews, PLLC

(57) ABSTRACT

A medical device includes a sheath defining a lumen, a first elongate member, and a second elongate member. The first and second elongate members are movably disposed within the lumen. The medical device further includes a basket comprising a plurality of legs and a mesh portion. A proximal end of each leg of the plurality of legs is connected to the first elongate member, and a proximal end of the mesh portion is connected to the second elongate member.

14 Claims, 3 Drawing Sheets

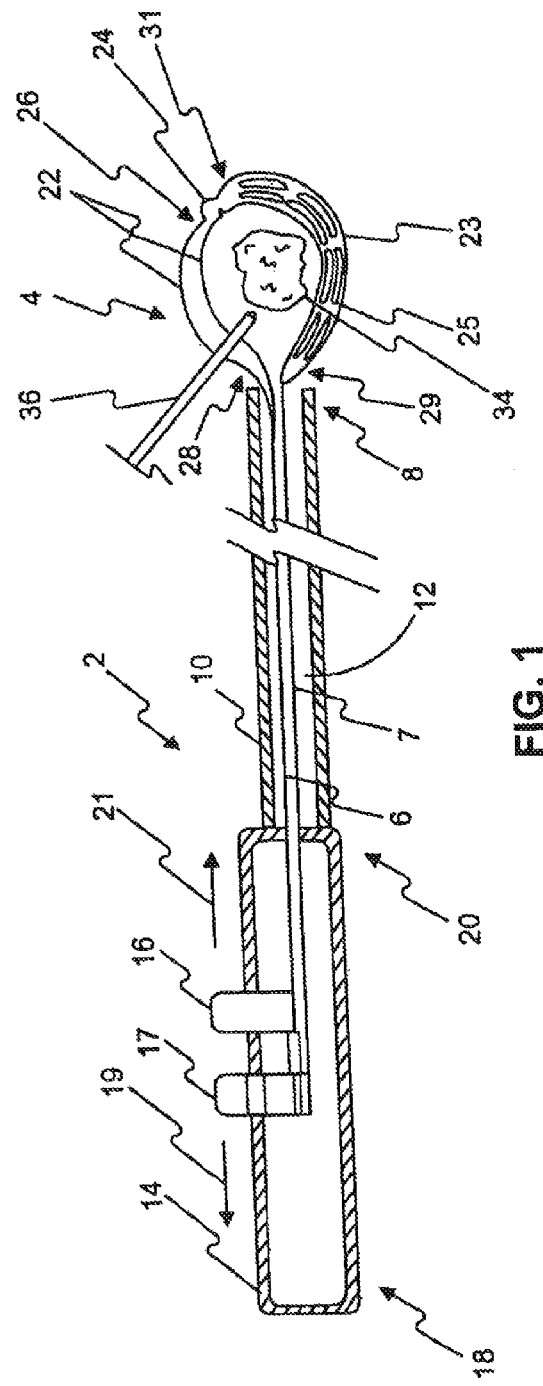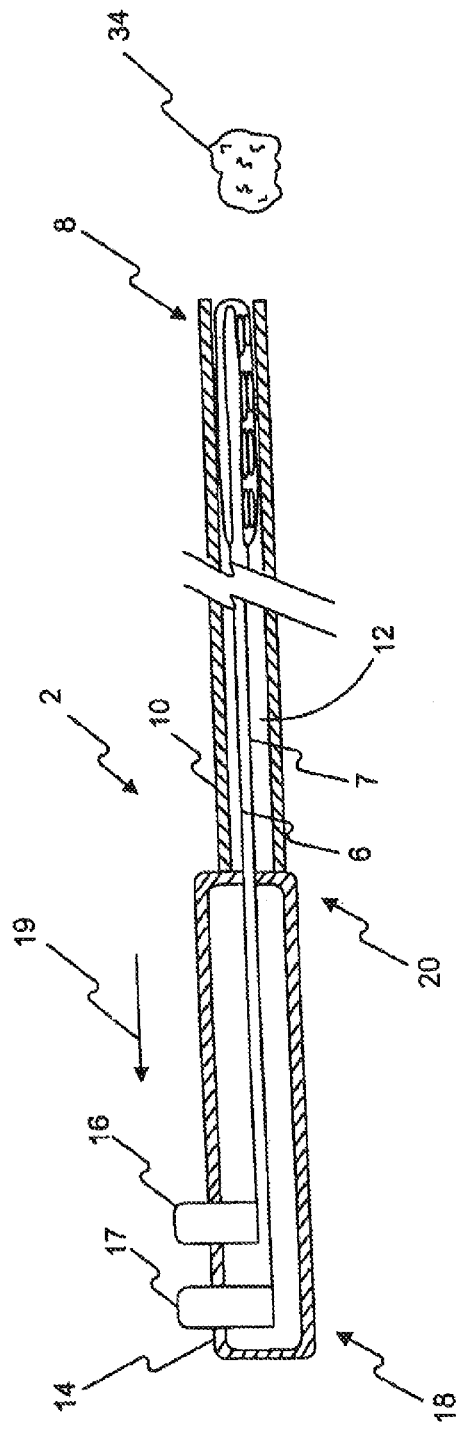

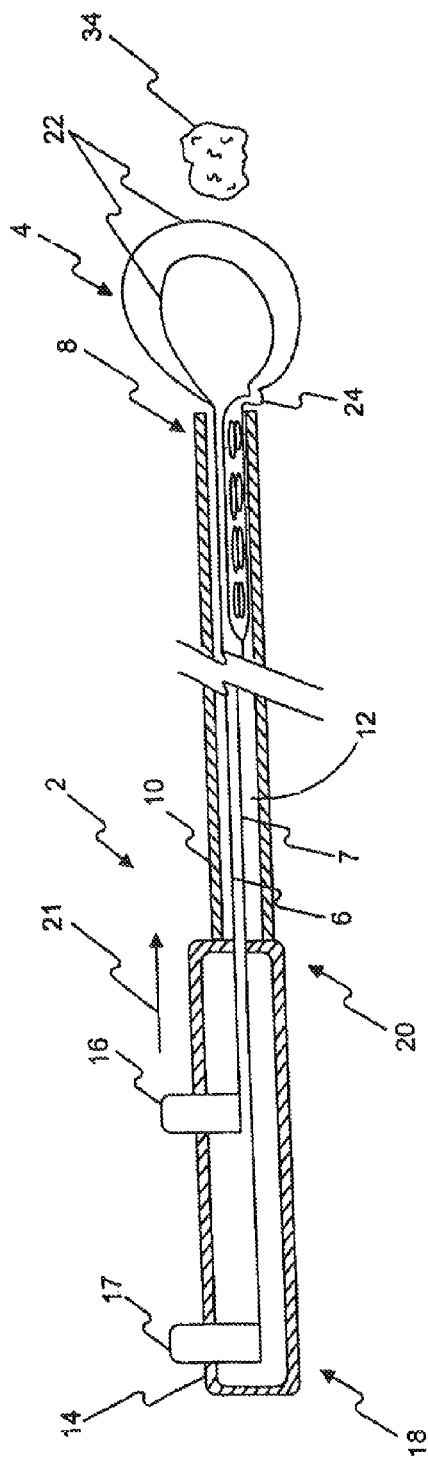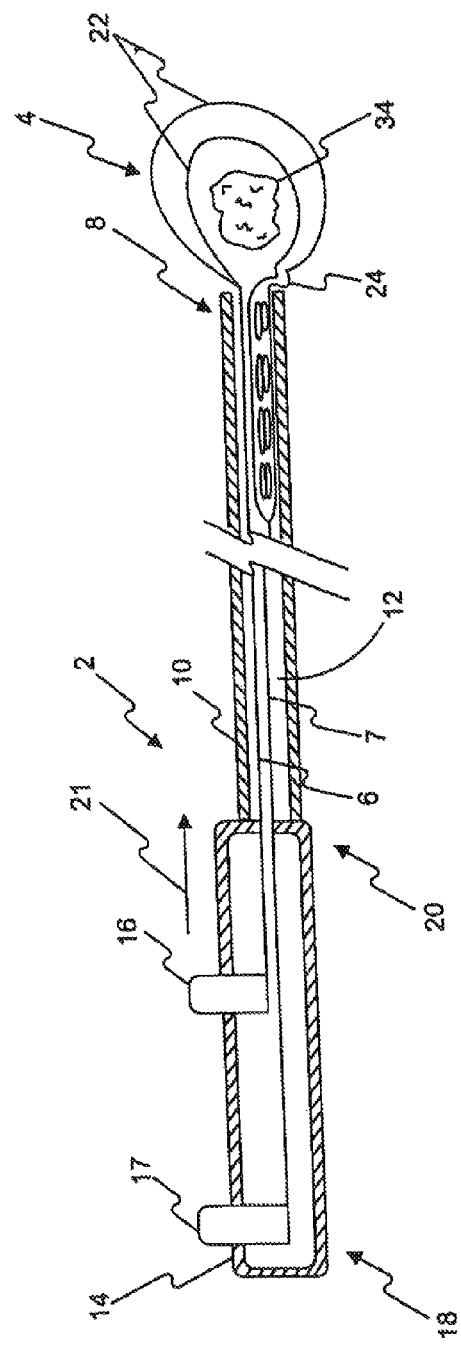

STEERABLE STONE BASKET

PRIORITY DATA

This application is a continuation of copending U.S. application Ser. No. 12/213,265, filed Jun. 17, 2008, which claims the benefit of U.S. Provisional Patent Application No. 60/960,950 filed Oct. 22, 2007, the complete disclosure of which both applications are incorporated by reference herein.

FIELD OF THE INVENTION

This disclosure relates generally to a medical device and, more particularly, to retrieval devices having steerable baskets and methods of manufacturing and using the same.

BACKGROUND OF THE INVENTION

Extractors have been used for the removal of stones, calculi, and other foreign matter from within the body. One type of extractor has a sheath and includes a basket at its distal end. The basket may be collapsed within the sheath to achieve a reduced diameter profile. The basket also may be opened when it extends beyond the sheath. Once opened, a targeted stone may be captured within the basket. The baskets of such extractors may include wires that are joined via soldering or welding to form a tip at a distal end of the basket. The wires may be joined to an elongate member at a proximal end of the basket, and the elongate member may be moveable relative to the sheath in order to expand and collapse the basket. Manufacturing such devices, however, can be costly and time consuming. In addition, it may be difficult to capture a targeted stone within such a basket without pushing the stone deeper into the body cavity in which the stone is located. It also may be difficult to capture small stone fragments formed when the targeted stone is broken up through processes such as laser lithotripsy.

The present disclosure provides retrieval devices and methods of manufacturing and using the same that avoid some or all of the aforementioned shortcomings of existing devices.

SUMMARY OF THE INVENTION

In an exemplary embodiment of the present disclosure, a medical device includes a sheath defining a lumen, a first elongate member, and a second elongate member. The first and second elongate members are movably disposed within the lumen. The medical device further includes a basket comprising a plurality of legs and a mesh portion. A proximal end of each leg of the plurality of legs is connected to the first elongate member, and a proximal end of the mesh portion is connected to the second elongate member.

In accordance with certain embodiments of the present disclosure, the device may include one or more of the following features. For example, the basket is formed from a single piece of a material. In such an embodiment, the plurality of legs is formed by removing portions of the single piece of material, and the mesh portion is formed by removing portions of the single piece of material. The mesh portion comprises a plurality of slots formed by removing portions of the single piece of material, and the single piece of material comprises a shape memory material and a cannula.

In other exemplary embodiments, the basket further includes an atraumatic tip, and the first elongate member is moveable independent of the second elongate member. In such embodiments, movement of the first elongate member actuates the plurality of legs independent of the mesh portion, and movement of the second elongate member actuates the mesh portion independent of the plurality of legs. In addition, the plurality of legs comprises two legs, and the plurality of legs and the first elongate member are formed from a single piece of material. In such embodiments, the mesh portion is formed from the single piece of material. A distal end of each of the plurality of legs is connected to a distal end of the mesh portion, and the proximal end of each of the plurality of legs is not connected to the proximal end of the mesh portion.

In further exemplary embodiments, the plurality of legs has a legs expanded position in which the plurality of legs is disposed substantially outside of the lumen and a legs collapsed position in which the plurality of legs is disposed substantially within the lumen, and wherein the mesh portion has a mesh expanded position in which the mesh portion is disposed substantially outside of the lumen and a mesh collapsed position in which the mesh portion is disposed substantially within the lumen. In such embodiments, the mesh portion is configured to maintain the mesh collapsed position while the plurality of legs is in the legs expanded position. In addition, the plurality of legs is configured to maintain the legs collapsed position while the mesh portion is in the mesh expanded, position, at least a portion of the plurality of legs is distal the mesh when the plurality of legs is in the legs expanded position, and at least a portion of the mesh portion is distal the plurality of legs when the mesh portion is in the mesh expanded position.

In another exemplary embodiment of the present disclosure, a medical retrieval device basket includes a plurality of legs and a mesh portion disposed substantially opposite the plurality of legs. The plurality of legs and the mesh portion are formed from a single piece of material, and the plurality of legs is moveable independent of the mesh portion.

In accordance with certain embodiments of the present disclosure, the device basket may include one or more of the following features. For example, the plurality of legs is formed by removing portions of the single piece of material, and the mesh portion is formed by removing portions of the single piece of material. The mesh portion comprises a plurality of slots formed by removing portions of the single piece of material, and the single piece of material comprises a shape memory material and a cannula. The basket further includes an atraumatic tip. In other exemplary embodiments, each of the plurality of legs is connected to a first elongate member, and the mesh portion is connected to a second elongate member.

In a further exemplary embodiment of the present disclosure, a method of manufacturing a medical device basket includes removing first portions of a piece of material to form a plurality of legs and removing second portions of the piece of material to form a mesh portion disposed substantially opposite the plurality of legs.

In accordance with certain embodiments of the present disclosure, the method may include one or more of the following features. For example, removing first portions of the piece of material and removing second portions of the piece of material includes one of laser cuffing, chemical etching, die cutting, and mechanically slicing. In addition, the first portions and the second portions are substantially longitudinal portions, and the plurality of legs comprises two legs. In other exemplary embodiments, the method further includes connecting each leg of the plurality of legs to a first elongate member, connecting the mesh portion to a second elongate member, and forming an atraumatic tip at a distal end of the basket.

In still another exemplary embodiment of the present disclosure, a method of removing matter from the body of a patient includes providing a medical device including a sheath defining a lumen, a first elongate member and a second elongate member, the first and second elongate members being movably disposed within the lumen, and a basket comprising a plurality of legs and a mesh portion, a proximal end of each leg of the plurality of legs being connected to the first elongate member, and a proximal end of the mesh portion being connected to the second elongate member. The method further includes advancing the medical device to a treatment site within the body of the patient, capturing the matter within the basket of the device, and removing the medical device from the body of the patient.

In accordance with certain embodiments of the present disclosure the method may include one or more of the following features. For example, in certain embodiments, capturing the matter further includes advancing the first elongate member in a distal direction. In such an embodiment, advancing the first elongate member includes at least partially extending the plurality of legs substantially outside of the lumen while maintaining the mesh portion substantially within the lumen. Advancing the first elongate member also includes forming a substantially open basket with the plurality of legs distal to the stone. Capturing the matter also includes advancing the device in the distal direction once the elongate member has been advanced, and advancing the second elongate member in the distal direction.

In another exemplary embodiment, advancing the second elongate member includes at least partially extending the mesh portion substantially outside of the lumen while maintaining at least a portion of the plurality of legs outside of the lumen. In such an embodiment, advancing the second elongate member also includes substantially encircling the stone with the mesh portion, and capturing the matter further includes partially retracting the first elongate member in a proximal direction.

In still another exemplary embodiment, capturing the matter further includes forming a backstop with the mesh portion. The method also includes reducing the size of the matter and sweeping at least a portion of the matter from the treatment site with the mesh portion.

It is to be understood that both the foregoing general description and the following detailed description are exemplary and explanatory only, and are not restrictive of the invention as claimed.

BRIEF DESCRIPTION OF THE DRAWINGS

FIG. 1 is a partial cross-sectional view of a retrieval device according to an exemplary embodiment of the present disclosure.

FIG. 2 illustrates an alternate configuration of the device of FIG. 1.

FIG. 3a illustrates another configuration of the device of FIG. 1.

FIG. 3b illustrates still another configuration of the device of FIG. 1.

DETAILED DESCRIPTION

Figure 4:
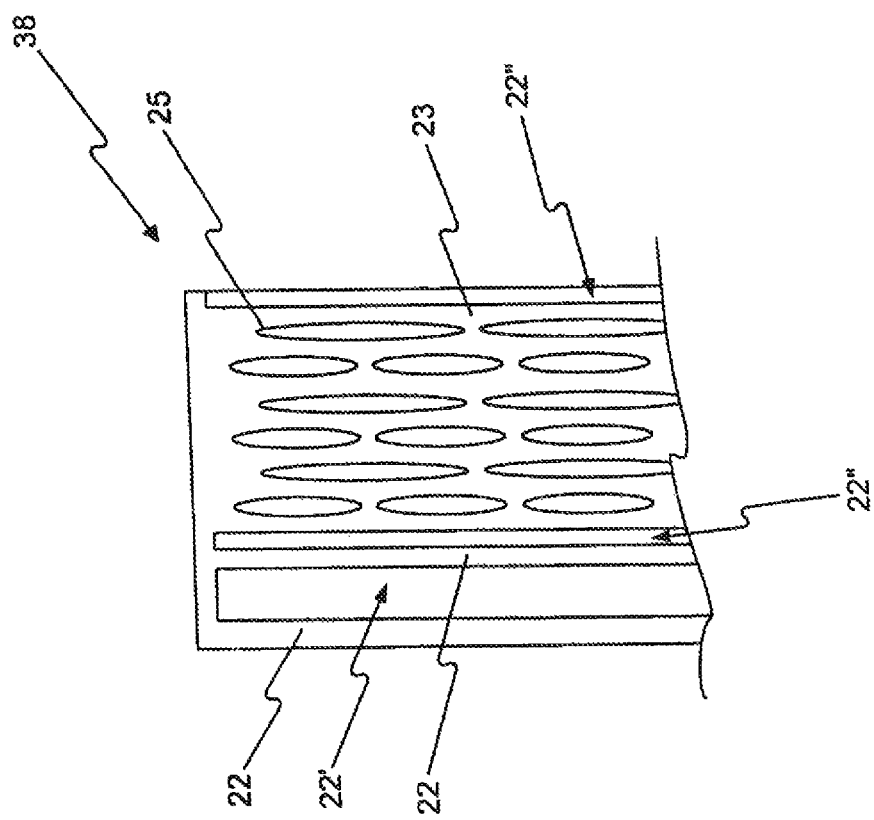
FIG. 4 is a side view of a portion of an unformed basket of the device of FIG. 1.

Exemplary embodiments of the present disclosure are illustrated in the accompanying drawings. Wherever possible, the same reference numbers will be used throughout the drawings to refer to the same or like parts.

In an exemplary embodiment of the present disclosure, a retrieval device includes a plurality of legs and a mesh portion. The legs and the mesh portion are independently moveable, and together, the legs and mesh portion form an asymmetric steerable basket at a distal end of the retrieval device useful for capturing and removing matter, such as a stone, from within the body of a patient. The legs may be configured to extend from a distal end of a sheath of the retrieval device while the mesh portion remains within a lumen of the sheath. Thus, the legs may move distal the mesh portion and may form a substantially open basket face proximal the targeted stone. The legs and/or the retrieval device may be manipulated so as to at least partially capture the stone within the substantially open basket without forcing the stone further into the body cavity in which it is located. Once the stone is at least partially captured, the mesh portion may be deployed from the distal end of the sheath to encircle the stone and, in some embodiments, the legs may be at least partially retracted. Once the legs are partially retracted, at least a portion of the mesh portion may extend distal the legs. The mesh portion may be used as, for example, a backstop during stone fragmentation and/or reduction processes. The mesh portion may also be used to sweep, for example, stone fragments from the body of the patient after such processes.

FIG. 1 illustrates a retrieval device 2 according to an exemplary embodiment of the present disclosure. The device 2 includes a basket 4, a first elongate member 6, and a second elongate member 7. The device 2 further includes a sheath 10 defining a lumen 12, and the first and second elongate members 6, 7 are movably disposed within the lumen 12. Relative movement between the first and second elongate members 6, 7 and the sheath 10 assists the basket 4 in forming an expanded position (shown in FIG. 1), where the basket 4 is disposed beyond a distal end 8 of the sheath 10, and a retracted position (shown in FIG. 2), where the basket 4 is disposed within the lumen 12 of the sheath 10.

The basket 4 may include a plurality of legs 22. The plurality of legs 22 may include any number of legs useful in immobilizing, capturing and/or retrieving a targeted stone 34, calculi, or other foreign matter. As shown in FIG. 1, in an exemplary embodiment, the plurality of legs 22 may include two legs. Because, as will be described below, the portion of the basket 4 having legs 22 may be used to initially encircle the stone 34, it is preferred to minimize the number of legs 22 in at least certain embodiments.

The proximal end 28 of each leg of the plurality of legs 22 may be connected to a distal end of the first elongate member 6 in any conventional way. Alternatively, the plurality of legs 22 may be formed of the same piece of material as the first elongate member 6.

The basket 4 may also include a mesh portion 23 disposed substantially opposite the plurality of legs 22. The mesh portion 23 may define a plurality of openings, orifices, or slots 25. As described above with respect to the plurality of legs 22, the mesh portion 23 may be useful in immobilizing, capturing, and/or retrieving the targeted stone 34, and the plurality of slots 25 may be sized, angled, and/or otherwise configured to permit, for example, fluids to pass through the basket 4 while retaining a captured stone 34. The proximal end 29 of the mesh portion 23 may be connected to a distal end of the second elongate member 7 in any conventional way. Alternatively, the mesh portion 23 may be formed of the same piece of material as the second elongate member 7. In an exemplary embodiment, the plurality of legs 22 and the mesh portion 23 may be formed of the same piece of material. In such an embodiment, one or both of the first and second elongate members 6, 7 also may be formed of the same piece of material. As will be discussed below, the piece of material may be, for example, a cannula comprising any conventional shape memory material. Such materials may include, for example, nitinol.

The basket 4 may further include an atraumatic tip 24. The atraumatic tip 24 may be disposed at a distal end of the basket 4, and the atraumatic tip 24 may be connected to the distal end 26 of each of the plurality of legs 22 and the distal end 31 of the mesh portion 23. The atraumatic tip 24 may have any atraumatic configuration known in the art. For example, the atraumatic tip 24 may be a filled, crimped, and/or capped distal end 26 of the plurality of legs 22. Alternatively, the atraumatic tip 24 may be a filled, crimped, and/or capped distal end 31 of the mesh portion 23.

The device 2 also may include a handle 14 configured to assist in transitioning the basket 4 between the expanded position and the retracted position. The handle 14 may include, for example, a first slide 16, a second slide 17, and/or other conventional mechanisms configured to assist in manipulating the position of the basket 4. In an exemplary embodiment, moving the first and second slides 16, 17 toward a distal end 20 of the handle 14 (in the distal direction of arrow 21) may move the first and second elongate members 6, 7, respectively, and the basket 4 in a distal direction relative to the handle 14 and, thus, may assist in transitioning the basket 4 to the expanded position shown in FIG. 1. In such an embodiment, moving the first and second slides 16, 17 toward a proximal end 18 of the handle 14 (in the proximal direction of arrow 19) may move the first and second elongate members 6, 7, respectively, and the basket 4 in a proximal direction relative to the handle 14 and, thus, may assist in transitioning the basket 4 to the retracted position shown in FIG. 2. In this exemplary embodiment, the sheath 10 may remain stationary with respect to the handle 14. As will be explained below, the first and second slides 16, 17 and the first and second elongate members 6, 7 may be configured to enable the user to manipulate the plurality of legs 22 independent of the mesh portion 23, and manipulate the mesh portion 23 independent of the plurality of legs 22. In such an embodiment, the basket 4 may be desirably steerable, and the device 2 may be used to capture a targeted stone 34 within the body of a patient.

Each of the first and second elongate members 6, 7 may be formed from, for example, a wire, rod, tube, hypotube, cannula, stent, or other piece of biocompatible material or combination of biocompatible materials known in the art. Such materials may include, but are not limited to, polyamide, PEBAX, stainless steel (such as 300 and 400 series), cobalt, chromium, nickel, titanium, nitinol, thermoforming plastic, polytetrafluoroethylene ("PTFE"), and expanded polytetrafluoroethylene ("ePTFE"). The first and second elongate members 6, 7 may comprise a shape memory material. The first and second elongate members 6, 7 may also be a metal coated with a polymer and may have one or more layers of material. The first and second elongate members 6, 7 may be solid or hollow, and may be substantially cylindrical. Alternatively, the first and second elongate members 6, 7 may be formed from a flat sheet of material. If formed from a flat sheet, the first and second elongate members 6, 7 may be formed into a substantially cylindrical shape. As previously stated, in an exemplary embodiment, the plurality of legs 22, the mesh portion 23, and/or one or both of the first and second elongate members 6, 7 may be formed from the same piece of material, and the piece of material may be any of the materials discussed above with respect to the first and second elongate members 6, 7.

The overall length and diameter of the first and second elongate members 6, 7 may vary depending on the application. For example, relatively long first and second elongate members 6, 7 (and therefore a relatively long device 2) may be advantageous for retrieving stones or other calculi deep within the body of the patient. In addition, first and second elongate members 6, 7 having a relatively small diameter (and a correspondingly small diameter sheath 10) may be advantageous for retrieving stones from restricted passageways within the human urinary tract. The first and second elongate members 6, 7 may be relatively flexible to facilitate the retrieval of stones located in complex, tortuous body structures.

The sheath 10 may be formed from any, of the materials discussed above with respect to the first and second elongate members 6, 7. Although FIGS. 1-3 illustrate a sheath 10 having a single lumen 12, in additional exemplary embodiments of the present disclosure, the sheath 10 may define more than one lumen 12. The additional lumen may be used for insertion of a lithotripsy device or other therapeutic or diagnostic device, or for irrigation or suction, for example. The sheath 10 may be dimensioned to fully enclose the first and second elongate members 6, 7 and the basket 4 when the basket 4 is in the retracted position shown in FIG. 2.

As illustrated in FIG. 4, the plurality of legs 22 and/or the mesh portion 23 of the basket 4 may be formed by, for example, laser cutting, chemical etching, die cutting, or mechanically slicing a single piece of material 38. FIG. 4 shows a flat piece of materials 38 having a number of cuts, openings, and/or slots therein. Material 38 may be rolled, twisted, or otherwise formed into the final basket 4. The single piece of material 38 may be the same piece of material as the first and second elongate members 6, 7. Alternatively, the single piece of material 38 may be a substantially hollow, substantially cylindrical wire, rod, tube, hypotube, cannula, stent, or other piece of biocompatible material connected to the first and second elongate members 6, 7.

The material 38 may be cut in, for example, a longitudinal direction to define the plurality of legs 22. For example, cut 22 defines the opening between the plurality of legs 22 and cuts 22" define the space between the plurality of legs 22 and the mesh portion 23. The width of the cuts may define the width and mechanical behavior of each leg of the plurality of legs 22, and the desired width may vary depending on the particular application. For example, it may be advantageous to have relatively narrow basket legs when retrieving a relatively large stone 34 from a body structure. The length of the longitudinal cuts may define the length and mechanical behavior of the plurality of legs 22, and the desired length may vary depending on the particular application. Each leg of the plurality of legs 22 may have the same length and width, or the length and width of each leg 22 may vary depending on the particular application. In addition, the spacing between the plurality of legs 22 may vary or may be consistent.

The material 38 may be cut in, for example, a longitudinal direction, a transverse direction, a V-shape, a wave-shape, a saw-shape, and/or any other shape or direction to define the mesh portion 23. The cuts may form the plurality of slots 25. As illustrated in the Figures, the slots 25 may extend substantially longitudinally along the basket 4. Alternatively, the slots 25 may extend at any angle relative to a longitudinal axis (not shown) of the basket 4. The number, size, and configuration of the slots 25 may correspond to the desired porosity of the mesh portion 23. For example, a mesh portion 23 having relatively long, wide, and/or numerous slots 25 may be more porous than a mesh portion 23 having relatively short, narrow, and/or few slots 25.

The plurality of legs 22 and/or the mesh portion 23 may be, for example, cold worked or heat processed to form a shape in memory. The shape of the plurality of legs 22 and/or the mesh portion 23 may be fully formed once the first and second elongate members 6, 7 are moved fully in the distal direction and the basket 4 is allowed to fully expand (as shown, for example, in FIG. 1). Alternatively, the shape may be partially formed when the basket 4 is partially expanded (as shown, for example, in FIGS. 3a and 3b). The resulting basket 4 may be any shape useful in capturing and/or retrieving a stone 34 or other calculi or foreign matter, and may be sized so as to be capable of capturing a stone 34 in the range of approximately 4 mm to approximately 10 mm along its largest dimension. Such baskets 4 may be, for example, substantially spherical or substantially lemon shaped.

The mesh portion 23 may be any webbing, netting, or other like structure. The structure is preferably porous, but may be nonporous. The material 38 (FIG. 4) of the structure may be, for example, nitinol, stainless steel, polyvinylethylene ("PVE"), polyvinyl alcohol ("PVA"), ePTFE, PTFE, foam, rubber, plastic, polyurethane, or any other, metal, polymer, or composite known in the art. The structure may allow, for example, fluid or other material to pass through while prohibiting, for example, stones from escaping the basket 4. If not formed of the same piece of material as the legs, the structure may be attached to the plurality of legs 22 through welding, grafting, tying, or any other attachment method known in the art.

The plurality of legs 22 and/or the mesh portion 23 of the basket 4 may also be coated with a sheet of protection material (not shown) to protect the plurality of legs 22 and/or the mesh portion 23 during processes such as, for example, laser lithotripsy. The configuration, material, and other characteristics of the basket 4 described herein permit the basket 4 to assume a contracted, collapsed state within the sheath 10 for delivery to a treatment site, and an expanded state for use at the treatment site.

At least some aspects of the present disclosure may be used, for example, to retrieve a stone 34, calculus, or other material from any location within the body, such as, for example, in the urinary tract of the patient. The device 2 may be inserted through the urethra of the patient or, alternatively, the device 2 may be inserted percutaneously to a treatment site. The treatment site within the body may correspond to the location of a targeted stone 34.

The stone 34 targeted for retrieval may be a kidney stone, a struvite, a uric acid stone, a cystine stone, or other solid deposit commonly removed from a body structure or passageway within the body. Such stones 34 may contain various combinations of chemicals, including, but not limited to, calcium, oxalate, and phosphate. The stone 34 may be of any size and could have a length or diameter of approximately 1 mm to 12 mm. These lengths and diameters are merely exemplary, and aspects of the present disclosure may assist in the retrieval of stones larger or smaller than those discussed herein. Stones 34 may be of any shape and could be, for example, flat, round, smooth, or jagged. The device 2 may retrieve stones 34 that are both impacted and free floating.

The device 2 may be advanced to the treatment site through an access sheath (not shown), stent, or other access or dilatation device known in the art. In addition, the device 2 may be used in conjunction with an endoscope (not shown) or other type of intracorporeal scope known in the art. The endoscope may advance through the body over a guidewire to the treatment site. Alternatively, the endoscope may be independently fed to the treatment site without the use of a guidewire. Once the treatment site has been reached, the device 2 may be fed through an access port of the endoscope to gain access to the stone 34.

While being advanced to the treatment site, the basket 4 of the device 2 may be at least partially, and preferably fully, enclosed within the sheath 10. This configuration (shown in FIG. 2) may minimize the size of the device 2 and may assist in advancing the device 2 through the endoscope. Upon exiting the endoscope and accessing the stone 34, the user may extend at least a portion of the basket 4 from the distal end 8 of the sheath 10. In an exemplary embodiment, the user may move the first slide 16 in the distal direction of arrow 21, thereby moving the first elongate member 6 in the distal direction of arrow 21 (as shown in FIG. 3a). Such movement may force at least a portion of the plurality of legs 22 to exit the distal end 8 of the sheath 10. This presents a substantially open distal, or front, face of the basket 4 to the stone 34. The user may manipulate the device 2, such as pushing the device 2 distally, such that the plurality of legs 22 may at least partially capture the stone 34 as shown in FIG. 3b. The mesh portion 23 may remain fully or at least partially within the sheath 10 while the plurality of legs 22 is extended. As mentioned above, using only the plurality of legs 22 to partially capture the stone 34 may enable the user to surround the stone 34 with a partially formed and substantially open-ended basket 4. Using the substantially open-ended basket configuration of FIGS. 3a and 3b may also enable the user to avoid pushing the stone 34 out of reach of the basket 4 while the basket 4 is transitioned from the collapsed position to the expanded position. Thus, unlike existing baskets, the exemplary asymmetric steerable baskets 4 of the present disclosure do not require the user to maneuver the atraumatic tip 24 of the basket 4 distal the stone 34 prior to capturing the stone 34. This is advantageous because such maneuvering may be difficult, if not impossible, in narrow body passages. In addition, in maneuvering the tip of a basket distal a stone prior to capturing the stone, the user may inadvertently push the stone further into the body passage in which it is located, thereby making it more difficult to remove the stone. The exemplary baskets 4 of the present disclosure avoid at least some of these disadvantages.

Once the stone 34 is at least partially captured by the plurality of legs 22, the user may move the second slide 17 in the direction of arrow 21, thereby moving the second elongate member 7 in the distal direction of arrow 21 (as shown in FIG. 1). Such movement may force at least a portion of the mesh portion 23 to exit the distal end 8 of the sheath 10 to encircle the stone 34 and/or substantially fully capture the stone 34 within the basket 4. The user may also partially retract the first slide 16 and first elongate member 6 by moving the first slide 16 in the proximal direction of arrow 19 (as shown in FIG. 1). Such movement may assist the user in capturing and/or immobilizing the stone 34 once the mesh portion 23 has been fully deployed. Once captured, the stone 34 may be retrieved by removing the device 2 from the body of the patient.

If, however, the targeted stone 34 is larger than approximately 3 mm, the stone 34 may be too large to be safely removed from the body. In these situations, the user may use the device 2 to capture and assist in immobilizing the stone 34. The user may then perform a stone-reduction process, such as, for example, laser lithotripsy, to break up or otherwise reduce the size of the stone 34. The basket 4, and in particular, the mesh portion 23, may act as a backstop during such a process and may assist in preventing particles of the stone 34 from migrating or escaping from the treatment site during or after the stone-reduction process. In such a process, a laser fiber 36 (FIG. 1) or other conventional device may be used to break up the stone 34. The laser fiber 36 may be fed through an access port of an endoscope and may be activated and controlled by the user to reduce the size of the stone 34 or to fragment it into smaller pieces. Once the stone 34 has been fragmented, the mesh portion 23 may substantially immobilize the stone fragments and stop them from passing further distally. As shown in FIG. 1, at least partially retracting the plurality of legs 22 may cause the mesh portion 23 to more fully surround the stone 34 to assist in substantially immobilizing the fragments. Moreover, once the stone 34 has been fragmented, the mesh portion 23 may act as, for example, a net or sweeping device to sweep stones and stone particles obtained from the reduction process out of the body.

Alternatively, the user may decide to release the stone 34 after the stone 34 has been captured. In such a situation, the user may move the first elongate member 6, and consequently, the plurality of legs 22, in the direction of arrow 21. With the plurality of legs 22 substantially fully extended in the distal direction, the user may at least partially retract the mesh portion 23 by moving the second elongate member 7 in the direction of arrow 19. Manipulating the first and second elongate members 6, 7 in this manner may substantially open the basket 4. The user may then move the entire device 2 in the direction of arrow 19 such that the captured stone 34 may be easily released. Because, for example, the atraumatic tip 24 will not interfere with the position of the stone 34 as the stone 34 is released from the basket 4, it may be safer and/or easier to release a captured stone 34 from the baskets 4 of the present disclosure than from other known baskets.

Other embodiments of the invention will be apparent to those skilled in the art from consideration of the specification and practice of the invention disclosed herein. For example, the first and second elongate members 6, 7 and/or the sheath 10 may include a plurality of flexibility features configured to increase the flexibility of the device 2. The flexibility features may be formed by removing a portion of the first and second elongate members 6, 7 and/or the sheath 10. It is intended that the specification and examples be considered as exemplary only, with the true scope and spirit of the invention being indicated by the following claims.

What is claimed is:

1. A method of removing matter from the body of a patient with a medical device including a basket having a plurality of legs and a mesh portion, the method comprising:
    advancing the medical device to a treatment site within the body of the patient; and
    capturing the matter within the basket of the medical device by moving a first proximal end of the basket relative to a second proximal end of the basket,
    wherein the moving includes advancing the first proximal end of the basket distally so that the plurality of legs extend outside of a lumen of a sheath, while maintaining the mesh portion fully within the lumen of the sheath.

2. The method of claim 1, wherein the moving includes moving the first proximal end with a first actuator coupled to the first proximal end.

3. The method of claim 2, wherein the moving further includes moving the second proximal end with a second actuator coupled to the second proximal end.

4. The method of claim 1, wherein the advancing of the first proximal end includes forming a substantially open basket with the plurality of legs proximal to the matter.

5. The method of claim 4, wherein the capturing further includes advancing the medical device in a distal direction after the advancing of the first proximal end.

6. The method of claim 5, wherein the capturing further includes advancing the second proximal end in the distal direction to at least partially extend the mesh portion outside of the lumen while maintaining at least a portion of the plurality of legs outside the lumen.

7. The method of claim 6, wherein the capturing of the matter further includes partially retracting the first proximal end proximally so that at least a portion of the plurality of legs are retracted into the lumen, and the mesh portion substantially encircles the matter.

8. The method of claim 1, wherein a distal most end of the plurality of legs is distal to a distal most end of the mesh portion during the capturing step.

9. A method of removing matter from the body of a patient with a medical device including a basket having a plurality of legs and a mesh portion, the method comprising:
    advancing the medical device to a treatment site within the body of the patient; and
    capturing the matter within the basket of the medical device by positioning the plurality of legs at a distalmost end of the basket, and thereafter, positioning the mesh portion at the distalmost end of the basket.

10. The method of claim 9, wherein the positioning of the plurality of legs includes moving a first actuator, the first actuator being coupled to the plurality of legs.

11. The method of claim 10, wherein the positioning of the mesh portion includes moving a second actuator, the second actuator being coupled to the mesh portion.

12. The method of claim 9, wherein the positioning of the plurality of legs forms a substantially open basket with the plurality of legs proximal to the matter.

13. The method of claim 12, wherein the capturing of the matter further includes advancing the medical device in the distal direction after positioning the plurality of legs.

14. The method of claim 9, wherein a distal most end of the plurality of legs is distal to a distal most end of the mesh portion during the capturing step.

* * * * *